US011602702B2

(12) United States Patent
Iida et al.

(10) Patent No.: US 11,602,702 B2
(45) Date of Patent: Mar. 14, 2023

(54) **METHOD FOR PRODUCING PURIFIED *SALACIA* GENUS PLANT EXTRACT, AND PURIFIED *SALACIA* GENUS PLANT EXTRACT**

(71) Applicant: FUJIFILM Corporation, Tokyo (JP)

(72) Inventors: Atsushi Iida, Tokyo (JP); Fumitaka Ueda, Tokyo (JP); Hitomi Saito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 338 days.

(21) Appl. No.: 16/832,098

(22) Filed: Mar. 27, 2020

(65) Prior Publication Data

US 2020/0222831 A1 Jul. 16, 2020

Related U.S. Application Data

(63) Continuation of application No. PCT/JP2018/034595, filed on Sep. 19, 2018.

(30) Foreign Application Priority Data

Sep. 29, 2017 (JP) .............................. JP2017-189744
Jan. 29, 2018 (JP) .............................. JP2018-012452

(51) Int. Cl.
 *B01D 11/02* (2006.01)
 *A23L 27/10* (2016.01)
 *B01J 20/20* (2006.01)

(52) U.S. Cl.
 CPC .......... *B01D 11/0288* (2013.01); *A23L 27/11* (2016.08); *B01J 20/20* (2013.01)

(58) Field of Classification Search
 CPC .................. A23L 27/11; A23L 33/105; A61K 2236/00; A61K 36/37; A61P 3/10; A61P 13/02; A61P 17/00; A61P 19/02; A61P 29/00; A61P 43/00; B01D 11/0288; B01J 20/20
 See application file for complete search history.

(56) References Cited

U.S. PATENT DOCUMENTS

| | | | |
|---|---|---|---|
| 10,398,745 B2 | 9/2019 | Oda et al. | |
| 2002/0041904 A1 | 4/2002 | Yamahara | |
| 2011/0108486 A1* | 5/2011 | Schneider | C01B 7/14 210/668 |
| 2015/0141355 A1 | 5/2015 | Deshpande et al. | |

FOREIGN PATENT DOCUMENTS

| | | |
|---|---|---|
| CN | 105744942 A | 7/2016 |
| EP | 2510797 A1 | 10/2012 |
| JP | 7-41425 A | 2/1995 |
| JP | 11-29472 A | 2/1999 |
| JP | 11-103817 A | 4/1999 |
| JP | 11-137211 A | 5/1999 |
| JP | 3030008 B2 | 4/2000 |
| JP | 2006-188463 A | 7/2006 |
| JP | 2008-280282 A | 11/2008 |
| JP | 2011-157306 A | 8/2011 |
| JP | 2012-55205 A | 3/2012 |
| JP | 2013-70687 A | 4/2013 |
| JP | 6118888 B1 | 4/2017 |
| JP | 2017-132763 A | 8/2017 |

OTHER PUBLICATIONS

Machine translation of Deng et al (CN 101973985) published Feb. 16, 2011).*
Sellamuthu, P.S. et al., 2013, Journal of Medicinal Food, 16(8), 719-727.*
Matsuda, H. et al., 1999, Chemical and Pharmaceutical Bulletin, 47(12), 1725-1729 [Office action cites p. 1725].*
Australian Examination Report No. 1, dated Apr. 1, 2021, for corresponding Australian Application No. 2018343065.
Extended European Search Report for corresponding European Application No. 18863045.3, dated Oct. 14, 2020.
Yoshikawa et al., "Polyphenol Constituents from *salacia* Species: Quantitative Analysis of Mangiferin with α-Glucosidase and Aldose Reductase Inhibitory Activities," Yakugaku Zasshi, vol. 121, No. 5, 2001, pp. 371-378.
Japanese Office Action for corresponding Japanese Application No. 2019-544997, dated Mar. 2, 2021, with English translation.
Author Unknown, Food Style 21, vol. 6 No. 5, 2002, pp. 1-12, 6 pages total, with partial translation.
International Preliminary Report on Patentability and English translation of the Written Opinion of the International Searching Authority (Forms PCT/IB/326, PCT/IB/373, and PCT/ISA/237) for International Application No. PCT/JP2018/034595, dated Apr. 9, 2020.
International Search Report (Form PCT/ISA/210) for International Application No. PCT/JP2018/034595, dated Dec. 25, 2018, with English translation.
Yoshikawa et al., "Polyphenol Constituents from *salacia* Species: Quantitative Analysis of Mangiferin with α-Glucosidase and Aldose Reductase Inhibitory Activities", Yakugaku Zasshi, vol. 121, No. 5, 2001, pp. 371-378, 1st page Abstract.
Chinese Office Action and Search Report for corresponding Chinese Application No. 201880063002.1, dated Aug. 3, 2021, with an English translation.
Guo et al., "A new triucallane derivative from *Salacia hainanensis* Chun et How," Acta Pharmaceutica Sinica, vol. 44, No. 10, 2009, pp. 1123-1126, 4 pages total, with an English abstract.

(Continued)

*Primary Examiner* — Brian A McCaig

(74) *Attorney, Agent, or Firm* — Birch, Stewart, Kolasch & Birch, LLP

(57) ABSTRACT

Provided are a method for producing a purified *Salacia* genus plant extract having improved flavor by increasing the α-glucosidase inhibitory activity of the extract without significantly reducing the recovery rate of the extract concomitantly with purification; and a purified *Salacia* genus plant extract. The method for producing a purified *Salacia* genus plant extract includes an extraction step of bringing a *Salacia* genus plant-containing raw material extract including at least one of a *Salacia* genus plant, a *Salacia* genus plant extract, and a *Salacia* genus plant ground product, into contact with 0.1 to 20 mass % of activated carbon in the presence of an extraction solvent.

5 Claims, No Drawings

(56) References Cited

OTHER PUBLICATIONS

Chinese Office Action for corresponding Chinese Application No. 201880063002.1, dated Jul. 27, 2022, with an English translation.
Nie et al., "Progress in α-Glucosidase Inhibitor and Application Prospect of Inhibitors from Food," Academic Periodical of Farm Products Processing, 2012, pp. 18-23, 6 pages total, with an English abstract.
Chinese Office Action for Chinese Application No. 201880063002.1, dated Mar. 30, 2022, with English translation.
Office Action issued in Chinese Patent Application No. 201880063002.1, dated Jan. 12, 2023, with English translation.

* cited by examiner

METHOD FOR PRODUCING PURIFIED *SALACIA* GENUS PLANT EXTRACT, AND PURIFIED *SALACIA* GENUS PLANT EXTRACT

CROSS-REFERENCE TO RELATED APPLICATIONS

This application is a Continuation of PCT International Application No. PCT/JP2018/034595 filed on Sep. 19, 2018, which claims priority under 35 U.S.C. § 119(a) to Japanese Patent Application No. 2017-189744 filed on Sep. 29, 2017 and Japanese Patent Application No. 2018-012452 filed on Jan. 29, 2018. Each of the above application(s) is hereby expressly incorporated by reference, in its entirety, into the present application.

BACKGROUND OF THE INVENTION

1. Field of the Invention

The present disclosure relates to a method for producing a purified *Salacia* genus plant extract.

2. Description of the Related Art

Roots and stems of *Salacia* genus plants have been utilized as natural drugs in the traditional medicine Ayurveda of India and Sri Lanka. In Sri Lanka, it has been passed down that the root bark of *Salacia reticulata* is effective for the treatment of rheumatism, gonorrhea, and skin diseases, and that the above-mentioned root bark is used for the treatment of early stage diabetes mellitus.

In recent year, it has been reported that a *Salacia* genus plant extract has an effect of inhibiting a rise in the blood glucose level by a sugar absorption suppressing action based on α-glucosidase activity inhibition (for example, FOOD Style 21, Vol. 6, No. 5, pp. 72-78), and a *Salacia* genus plant extract includes various polyphenols (and mangiferin, which is xanthene glycoside) (for example, YAKUGAKU ZASSHI, 121(5), pp. 371-378).

These components are perceived as bitter taste, astringent taste, astringency, harsh taste, and odd taste, and there is a risk that these components may give unpleasant feeling to the consumers when ingested as foods.

Meanwhile, examples of a substance containing polyphenols similarly to the *Salacia* genus plant extract include a tea extract and a *Gymnema sylvestre* extract.

In JP2012-055205A, disclosed is a method for producing a purified green tea extract for the purpose of reducing flavonols without significantly impairing the recovery rate of catechins and thereby providing a purified green tea extract that is useful as a raw material for a catechin-containing beverage having excellent green tea flavor and easy to drink, the method including bringing an organic solvent aqueous solution of a green tea extract into contact with a particular amount of activated carbon for a predetermined time. In JP6118888B, disclosed is a method for producing a tea extract for the purpose of providing a method for producing a tea extract, by which a deep-bodied tea extract having satisfactory aftertaste and flavor is obtained, the method including an extraction step of extracting tea leaves in the presence of a particular amount of activated carbon. In JP2008-280282A, disclosed is a method for purifying a polyphenol-containing composition for the purpose of effectively performing bleaching with excellent safety without impairing the polyphenol content, and also providing a polyphenol-containing composition having unpleasant taste eliminated, with reduced precipitation, and having excellent flavor, the method including bringing a composition containing polyphenols into contact with activated carbon that has been treated at low temperature in advance.

Furthermore, in JP1999-137211A (JP-H11-137211A), disclosed is a *Gymnema sylvestre* essence having improved flavor, which is obtained by bringing the leaves of *Gymnema sylvestre* or an essence obtained by extracting the leaves into contact with activated carbon, and eliminating insoluble materials.

SUMMARY OF THE INVENTION

However, it was found that in order to obtain a *Salacia* genus plant extract that does not require processing into a pharmaceutical preparation, a food product, or the like and is appropriate for the use for oral intake, in a case in which a *Salacia* genus plant extract is purified by the treatments described in JP2012-055205A, JP6118888B, JP2008-280282A, and JP 1999-137211A (JP-H11-137211A) for the purpose of improving the flavor, the recovery rate of the *Salacia* genus plant extract and the α-glucosidase activity inhibitory action are decreased, and reduction of the flavor, particularly the odor and bitter taste characteristic of *Salacia* genus plants is insufficient.

A decrease in the recovery rate of a *Salacia* genus plant extract by purification is not preferable from the viewpoint of the production cost. Since a decrease in the α-glucosidase activity inhibitory action leads to a reduction in the activity of the *Salacia* genus plant extract, the one-time amount of intake should be increased, and therefore, there is a risk that the burden on the intaker may increase. Furthermore, in order to obtain an extract that can be directly taken in orally without being subjected to processing into a pharmaceutical preparation, a food product, or the like, it is important to produce an extract that has improved flavor and can be easily taken in.

According to an embodiment of the present invention, in view of the problems as described above, it is an object of the invention to provide a method for producing a purified *Salacia* genus plant extract having improved flavor while maintaining the α-glucosidase inhibitory activity of the extract, without significantly reducing the recovery rate of the extract concomitantly with purification.

Generally, since the raw material for obtaining a purified *Salacia* genus plant extract is at a high concentration compared to a tea extract or the like, the recovery rate can be easily decreased by purification, and therefore, purification treatment is not carried out.

However, the inventors of the present invention conducted a thorough investigation, and thereby the inventors clarified that a step of bringing a *Salacia* genus plant-containing raw material extract comprising at least one of a *Salacia* genus plant, a *Salacia* genus plant extract, and a *Salacia* genus plant ground product, into contact with 0.1 to 20 mass % of activated carbon, is effective in solving the problems described above. Furthermore, surprisingly, it was found that according to the production method of the present disclosure, the α-glucosidase inhibitory activity can be enhanced.

In this regard, the present inventors speculate as follows.

It is speculated that the flavor (odor and bitter taste) characteristic of *Salacia* genus plants is caused by the components (hereinafter, also referred to as "particular components") such as polyphenols and lipids contained in the *Salacia* genus plants. Since activated carbon has low affinity with active ingredients such as salacinol but has high affinity with these particular components, it is speculated that by performing a treatment with activated carbon that is brought into contact in a particular amount, the above-mentioned particular components are selectively removed, thus the content of the particular components included in the resulting purified *Salacia* genus plant extract is relatively reduced, and as a result, the flavor of the *Salacia* genus plant extract is improved.

It is considered that the α-glucosidase inhibitory activity effect, which has been slightly reduced as the particular components exert a certain action on the active ingredients such as salacinol, is increased by selective removal of the particular components, and as a result, the α-glucosidase inhibitory activity of the purified *Salacia* genus plant extract can be increased.

The speculation described above is not intended to limitedly analyze the effects of an embodiment of the invention but is intended to describe the embodiment as an example.

Specific means for solving the problems described above include the following embodiments.

[1] A method for producing a purified *Salacia* genus plant extract, the method comprising a step of bringing a *Salacia* genus plant-containing raw material extract comprising at least one of a *Salacia* genus plant, a *Salacia* genus plant extract, and a *Salacia* genus plant ground product into contact with 0.1 to 20 mass % of activated carbon.

[2] The method for producing a purified *Salacia* genus plant extract as described in [1], wherein the time for bringing the *Salacia* genus plant-containing raw material extract into contact with the activated carbon is 5 minutes to 5 hours.

[3] The method for producing a purified *Salacia* genus plant extract as described in [1] or [2], wherein water at 10° C. to 100° C. as the extraction solvent is used.

[4] The method for producing a purified *Salacia* genus plant extract as described in any one of [1] to [3], wherein the activated carbon has a specific surface area of 500 to 2,500 m$^2$/g and an average pore diameter of 0.5 to 10 nm.

[5] A purified *salacia* genus plant extract, produced by the production method as described in any one of [1] to [4].

[6] A purified *Salacia* genus plant extract, wherein the content of the sum of polyphenols and lipids with respect to the total amount of the purified *Salacia* genus plant extract is less than 10 mass %.

[7] The purified *Salacia* genus plant extract as described in [6], wherein the content of epicatechin with respect to the total amount of the purified *Salacia* genus plant extract is less than 0.004 mass %.

According to an embodiment of the present invention, a method for producing a purified *Salacia* genus plant extract, by which an odor characteristic of *Salacia* genus plants is improved while the α-glucosidase inhibitory activity of the extract is maintained, without significantly reducing the recovery rate of the extract concomitantly with purification; and a purified *Salacia* genus plant extract can be provided.

DESCRIPTION OF THE PREFERRED EMBODIMENTS

Hereinafter, an example of the embodiments of the invention will be explained. However, the present invention is not intended to be limited to the following embodiments, and modifications can be applied as appropriate within the scope of the purpose of the invention.

The numerical value range expressed using the symbol "~" according to the present specification means a range including the numerical values described before and after the symbol "~" as the minimum value and the maximum value, respectively.

With regard to a numerical value range described stepwise in the present specification, the upper limit or lower limit described in one numerical value range may be substituted for the upper limit or the lower limit of another numerical value range described stepwise.

Furthermore, with regard to the numerical value ranges described in the present specification, the upper limit or the lower limit of the numerical value range may be substituted for the values disclosed in Examples.

According to the present specification, the term "step" means not only an independent step; however, in a case in which a step cannot be clearly distinguished from other steps, as long as the predetermined purpose of the step is achieved, the step is included in the present term.

[*Salacia* Genus Plant-Containing Raw Material Extract]

*Salacia* genus plants are plants of the family Hippocrateaceae growing naturally mainly in Sri Lanka, India, and the South-East Asia region. Specific examples of a *Salacia* genus plant include one or more plants selected from *Salacia* reticulata, *Salacia* oblonga, *Salacia* prinoides, *Salacia* chinensis, *Salacia* latifolia, *Salacia* burunoniana, *Salacia* grandiflora, or *Salacia* macrosperma. The *Salacia* genus plant is preferably at least one plant selected from *Salacia* reticulata, *Salacia* oblonga, or *Salacia* chinensis.

According to the present disclosure, the term "*Salacia* genus plant-containing raw material extract" means components derived from a *Salacia* genus plant among the raw material for obtaining a purified *Salacia* genus plant extract in the extraction step, and other components included in the extract (for example, an extraction solvent used for preparing the raw material) are excluded.

According to the present disclosure, at least one of a *Salacia* genus plant, a *Salacia* genus plant extract, and a *Salacia* genus plant ground product may be used as the *Salacia* genus plant to be used for the *Salacia* genus plant-containing raw material extract. As the *Salacia* genus plant, edible parts such as roots, stems, leaves, flowers, and fruits of *Salacia* genus plants can be directly used.

According to the present specification, an extract of a *Salacia* genus plant and a ground product of a *Salacia* genus plant are used to mean to include an extract and/or ground product of edible parts such as roots, stems, leaves, flowers, and fruits of *Salacia* genus plants, and dried products of the extract and/or ground product. According to the present specification, a dried product may be a dried powder (essence powder). At the time of preparing the above-described extract and/or ground product of a *Salacia* genus plant, one or more kinds of sites of the *Salacia* genus plant may be used as a mixture. From the viewpoint of producing a purified *Salacia* genus plant extract efficiently, as the *Salacia* genus plant-containing raw material extract, preferably, an extract powder obtainable by drying a *Salacia* genus plant extract (essence) extracted from a site selected from roots and stems, or an essence powder obtainable by drying an essence is used.

A dried powder (essence powder) can be preferably obtained by extracting edible parts and the like of a *Salacia* genus plant by means of a solvent and drying an extract obtained as described above.

Examples of the solvent that is used for extraction include water, an alcohol, and a ketone, and a mixed solvent obtained by mixing two or more kinds of these may also be used.

Examples of the alcohol include methanol and ethanol, and ethanol is preferred.

Regarding the ketone, acetone, methyl ethyl ketone, cyclohexane, and the like are preferred.

Among those described above, water, an alcohol, a mixed solvent of water and an alcohol, or a mixed solvent of water and a ketone is preferred; water, an alcohol, or a mixed solvent of water and an alcohol is more preferred; and hot water at 50° C. to 98° C., ethanol, or a mixed solvent of water and ethanol is even more preferred.

The alcohol content in the mixed solvent of water and an alcohol is preferably 30 mass % to 90 mass %, and more preferably 40 mass % to 70 mass %.

The drying method used at the time of drying an extract and thereby obtaining a dried powder (essence powder) is not particularly limited, and known drying methods, for example, methods such as spraying drying and freeze-drying may be mentioned.

[Extraction Step]

The method for producing a purified *Salacia* genus plant extract of the present disclosure includes an extraction step of bringing a *Salacia* genus plant-containing raw material extract comprising at least one of a *Salacia* genus plant, a *Salacia* genus plant extract, and a *Salacia* genus plant ground product, into contact with 0.1 to 20 mass % of activated carbon in the presence of an extraction solvent.

{Activated Carbon}

The activated carbon to be used for the present disclosure can be used without any particular limitations on the type, characteristics, and the like of the activated carbon. Examples of the carbonaceous material of activated carbon include plant-based cokes of coconut shell, palm, fruit seeds, sawdust, *Eucalyptus*, pine, and the like; coal-based and petroleum-based cokes; carbides of pitches obtained by using those as raw materials; a phenolic resin, a vinyl chloride resin, and a vinylidene chloride resin; however, carbonaceous materials derived from plant-based materials such as coconut shell, palm, fruit seeds, sawdust, *Eucalyptus*, and pine are preferred.

Regarding the activated carbon, commercially available products can be used, and examples include SHIRASAGI (registered trademark) C, SHIRASAGI WH2c, SHIRASAGI W2c, SHIRASAGI WH2x, SHIRASAGI X7000H, SHIRASAGI X7100H, SHIRASAGI LGK-100, SHIRASAGI WHA, SHIRASAGI M, SHIRASAGI A, SHIRASAGI P, CARBORAFFIN, KYOURYOKU SHIRASAGI, SEISEI SHIRASAGI, TOKUSEI SHIRASAGI, granular SHIRASAGI LH2c, granular SHIRASAGI KL, granular SHIRASAGI MAC-W (all trade names, manufactured by Osaka Gas Chemicals Co., Ltd.); TAIKO S type (TAIKO S, TAIKO DP, TAIKO SA1000); and TAIKO K type (TAIKO K, TAIKO A, TAIKO KA, TAIKO M) (all trade names, manufactured by Futamura Chemical Co., Ltd.). Products obtained by subjecting these activated carbons to further purification treatment may also be used.

The average pore diameter of the activated carbon is preferably 0.5 to 10 nm, more preferably 1.0 to 10 nm, even more preferably 3.0 to 8.0 nm, and still more preferably 3.0 to 6.0 nm, from the viewpoint of obtaining a purified *Salacia* genus plant extract having further enhanced α-glucosidase activity inhibition.

The specific surface area of the activated carbon is preferably 500 to 2,500 $m^2/g$, more preferably 1,000 to 2,000 $m^2/g$, and even more preferably 1,200 to 1,800 $m^2/g$, from the viewpoint of increasing the recovery rate.

The detailed mechanism is not certainly understood; however, it is speculated that it is because the activity of a compound exhibiting α-glucosidase activity inhibition can be further increased as the activated carbon selectively removes particular components included in the *Salacia* genus plant extract.

Regarding the average pore diameter and specific surface area of the activated carbon, in a case in which the activated carbon is a commercially available product, the values described in catalogues can be employed. Furthermore, regardless of being a commercially available product or not, in a case in which these values are not clearly known, the values can be measured by the methods for measuring a specific surface area based on gas adsorption according to JIS Z 8830 (2013) and ISO 9277 (2010).

From the viewpoint of reducing bitter taste, the amount of the activated carbon to be contacted is preferably 0.20 mass % or more, more preferably 1.0 mass % or more, and even more preferably 3.0 mass % or more, with respect to the *Salacia* genus plant-containing raw material extract. Furthermore, from the viewpoint of increasing the recovery rate, the amount is preferably 15.0 mass % or less, and more preferably 10.0 mass % or less, with respect to the *Salacia* genus plant-containing raw material extract.

{Time for Contacting with Activated Carbon}

The time for contacting with activated carbon is preferably 5 minutes or longer, and more preferably 30 minutes or longer, from the viewpoint of efficiently obtaining a purified *Salacia* genus plant extract. From the viewpoint of obtaining a purified *Salacia* genus plant extract having further enhanced α-glucosidase activity inhibition, the time is preferably 5 hours or shorter, and more preferably 3 hours or shorter.

(Extraction Solvent)

Regarding the extraction solvent, any solvent can be used without any particular limitations on the type, characteristics, and the like thereof, and water and/or an organic solvent can be used; however, from the viewpoint of the production cost, the extraction solvent is preferably water. The type of water is not particularly limited, and water can be appropriately selected from tap water, distilled water, ion-exchanged water, natural water, and the like, and used.

Furthermore, in the case of using an organic solvent, for example, examples include alcohols such as ethanol and methanol; ketones such as acetone; and esters such as ethyl acetate. A hydrophilic organic solvent such as an alcohol or a ketone is preferred, and in consideration of the use in pharmaceutical preparations or food products, an alcohol is more preferred, while ethanol is even more preferred.

The extraction solvent may be the extraction solvent include in the *Salacia* genus plant-containing raw material extract described above. That is, the solvent used to prepare a *Salacia* genus plant extract (essence) that serves as a raw material may be used directly as the extraction solvent.

(Temperature)

The temperature at the time of contacting with activated carbon is preferably 10° C. to 100° C., more preferably 25° C. to 80° C., even more preferably 25° C. to 75° C., and still more preferably 30° C. to 65° C., from the viewpoint of increasing the α-glucosidase activity inhibition ability of the purified *Salacia* genus plant extract thus obtained.

{Means for Contacting with Activated Carbon}

Regarding the means for contacting with activated carbon, any known method can be employed without any particular limitations. For example, a batch method of adding an extraction solvent and activated carbon to an extract of a *Salacia* genus plant or a ground product of a *Salacia* genus plant, stirring the mixture to adsorb, and then collecting the activated carbon by a filtration operation; or a column method of using a column packed with activated carbon and bringing the mixture into contact by a continuous treatment, may be mentioned.

Since a batch system can easily realize contacting for a long time, the batch system can be preferably used from the viewpoint of productivity.

A method of adding an extraction solvent to a *Salacia* genus plant-containing raw material extract, subsequently gradually heating the extraction solvent, and then adding activated carbon is preferred from the viewpoint of productivity.

[Separation Step]

An extract obtained by performing the extraction step is subjected to one kind or a combination of two or more kinds of solid-liquid separation treatments selected from filtration, centrifugation, a precipitation treatment, a membrane treatment, or the like, thereby solid components of the *Salacia* genus plant and activated carbon are removed, and a purified *Salacia* genus plant extract can be obtained.

The method for filtration is not particularly limited, and for example, filtering separation by means of a filter paper, a metal filter, or a gas filter can be employed. The mesh size of the filter is not particularly limited as long as the solid components of the *Salacia* genus plant and the activated carbon can be reliably removed.

Centrifugation can be carried out using, for example, a known device such as a separation plate type, a cylindrical type, or a decanter type device, without any particular limitations. The use conditions (rotation speed and time) of centrifugation are not particularly limited as long as the solid components of the *Salacia* genus plant and the activated carbon can be reliably removed.

A membrane treatment is a treatment of passing through, for example, a membrane formed from a polymer material having a pore diameter of 10 μm or less, and examples of the form of the membrane include a flat membrane and a hollow fiber membrane.

In the separation step, from the viewpoint of increasing the purification efficiency, a concentration step of increasing the concentration of the extract obtained in the extraction step through concentrating or drying may be added, or a concentration step may be utilized in the middle of the separation step.

Through the production method of the present disclosure as described above, an odor and bitter taste characteristic of *Salacia* genus plants are reduced while the recovery rate and the α-glucosidase activity inhibition are maintained, and thus the content of the *Salacia* genus plant in the extract can be increased. As a result, a purified *Salacia* genus plant extract that can be orally taken in without being subjected to processing into a pharmaceutical preparation, a food product, or the like, can be obtained.

After the purified *Salacia* genus plant extract (purified essence) is obtained through the above-described extraction step, the essence may be concentrated (concentrated purified essence) or dried (purified essence powder). The concentration or drying method is not particularly limited, and known methods may be used.

Meanwhile, according to the present specification, the "recovery rate of the *Salacia* genus plant extract" or the "recovery rate" means the solid content, as expressed in percentage, of the purified *Salacia* genus plant extract with respect to the solid content of a *Salacia* genus plant extract obtainable without performing the extraction treatment described above. Meanwhile, the upper limit of the recovery rate is not particularly limited and may be 100 mass %.

The purified *Salacia* genus plant extract obtained by the production method of the present disclosure has excellent storage stability over time. Specifically, coloration and odor generation caused by storage at room temperature can be reduced. The detailed mechanism in this regard is not clearly understood; however, it is speculated that as the above-mentioned particular components are selectively removed, denaturation of the particular components caused by the influence of moisture in air concomitant with time lapse, or a reaction between the particular components and the active ingredients in the *Salacia* genus plant extract can be suppressed, the storage stability of the purified *Salacia* genus plant extract is improved.

[Purified *Salacia* Genus Plant Extract]

Since the purified *Salacia* genus plant extract of the present disclosure has improved flavor, the extract is an extract that can be orally taken in without being subjected to processing into a pharmaceutical preparation, a food product, or the like. Specifically, the odor and bitter taste characteristic of *Salacia* genus plants have been reduced, and the purified *Salacia* genus plant extract has characteristics as described below.

{Components}

In the purified *Salacia* genus plant extract, the contents of the sum of polyphenols and lipids are 0 mass % or more and less than 10 mass % in total with respect to the total amount of the purified *Salacia* genus extract.

According to the present specification, the polyphenols mean compounds that can be measured by the FOLIN-CIOCALTEU method according to ISO 14502-1 (2005), and examples include catechins. Furthermore, the lipids mean compounds that can be measured by an acid decomposition method, which is used for the analysis of lipids in a food product, and examples include cholesterol and glycerin.

Since the purified *Salacia* genus plant extract of the present disclosure has the polyphenols and lipids reduced as described above, the odor and bitter taste characteristic of *Salacia* genus plants are reduced, and the coloration and odor generation concomitant with storage over time can be reduced.

The purified *Salacia* genus plant extract may be dried (purified essence powder), may be produced into a powder with added excipients and the like, or may be subjected to a granulation treatment and produced into a granulation product having a large particle size. Regarding the excipients, the types, characteristics, and the like can be used without particular limitations.

The bitter taste of the purified *Salacia* genus plant extract can be judged by using the content of epicatechin among the polyphenols as an index. From the viewpoint of further reducing bitter taste, the content of epicatechin with respect to the total amount of the purified *Salacia* genus extract is preferably less than 0.004 mass %, and more preferably less than 0.003 mass %. Regarding the lower limit, for example, the content of epicatechin with respect to the total amount of the purified *Salacia* genus extract is 0.000 mass % or more.

(α-Glucosidase Activity Inhibition Ability)

The purified *Salacia* genus plant extract of the present disclosure has an α-glucosidase activity inhibition ability.

The sucrase 50% inhibition concentration ($IC_{50}$ value) as an index of the α-glucosidase inhibitory activity can be measured by the following method.

<Experiment method 1> Preparation of sample solution for measuring sucrase $IC_{50}$ value: 2 mg of a sample is measured into a tube, 2 mL of water is added thereto to suspend the sample, and thus a sample solution having a concentration of 1 mg/mL is created. This is diluted with water so as to obtain concentrations of 0, 50, 100, 250, and 500 μg/mL, respectively.

Preparation of substrate solution: Sucrose is dissolved in a 0.2 mol/L maleic acid buffer (pH 6.0) so as to obtain a sucrose concentration of 100 mmol/L, and this is used as a substrate solution.

Preparation of crude enzyme solution: 1 g of intestinal acetone powder rat (manufactured by SIGMA Corporation) is suspended in 10 mL of physiological saline, and the suspension is centrifuged (3,000 rpm, 4° C., 5 minutes). A supernatant thus obtained is separated and used as a crude enzyme solution.

400 μL of the substrate solution was added to 500 μL of each of the sample solutions of various concentrations described above, and the mixture was preliminarily heated in a water bath at 37° C. for 5 minutes. To each of these, 100 μL of the crude enzyme solution was added, and the mixtures were reacted for 60 minutes at 37° C. After completion of the reaction, the enzyme was deactivated by heating at 95° C. for 2 minutes, and thus the reaction was terminated. The glucose concentration thus produced is quantitatively analyzed using a commercially available Kit-Mutarotase Glucose Oxidase Method (GLUCOSE CII TEST WAKO, manufactured by Wako Pure Chemical Industries, Ltd.).

Preparation of blank: To 250 μL of each of the sample solutions of various concentrations described above, 200 μL of the substrate solution and 50 μL of the crude enzyme solution are added, and the mixture is immediately heated at 95° C. for 2 minutes to thermally deactivate the enzyme, and this is used as the blank data.

A calibration curve is produced from the values thus obtained, and the concentration at which 50% of the enzyme activity is inhibited ($IC_{50}$ value) is determined.

(Content of Salacinol)

The content of salacinol in the composition can be checked by detecting by high performance liquid chromatography under the following conditions.

Column: Shodex Asahipak NH2P-50 4E
Flow rate: 1 ml/min
Eluent: 80% acetonitrile
Oven temperature: 30° C.
Injection amount: 25 μL
Detector: Charged Aerosol Detector (CAD)

(Evaluation Results for Flavor by Taste Sensor)

The flavor of the purified *Salacia* genus plant extract of the present disclosure can be evaluated using a taste sensor.

The taste sensor according to the present disclosure is made to imitate a human taste detection system, and performs evaluation by measuring the responsiveness to a taste substance toward a sensor using an artificial lipid membrane.

In the artificial lipid membrane used in the sensor of a taste sensor, since the responding taste substance varies depending on the type of lipid, the mixing ratio of a plasticizer, and the like, different responsiveness to the basic five tastes such as sour taste, salty taste, sweet taste, bitter taste, and umami taste is exhibited by changing the type of the artificial lipid membrane. By utilizing this property, taste detection corresponding to each taste can be performed, and furthermore, in order to distinguish the foretaste and the aftertaste, the taste sensor can digitize and express taste through a plurality of items.

The artificial lipid membrane is stuck to the taste sensor surface, and as this membrane is immersed in a sample solution, there occurs a change in the membrane potential of the lipid membrane. As such, the amount of change in the membrane potential occurring in a case in which the taste substance included in a sample solution adsorbs to the sensor surface is treated as the sensor output value, and thereby the taste of the measurement sample can be judged comprehensively.

Regarding the measurement, first, a taste sensor is immersed into a solution that serves as a reference (hereinafter, also referred to as "reference solution"), and the membrane potential Vr is obtained. Next, as the taste sensor is immersed in a sample solution, the membrane potential Vs, which has changed as a result of an interaction with a taste substance, is obtained. From this difference (Vs−Vr), a relative value of the sensor output is calculated, and this is a value corresponding to the foretaste.

Regarding the aftertaste, after the foretaste is measured by the method described above, the taste sensor is simply prewashed with the reference solution and is immersed again in the reference solution, and the membrane potential Vr' is obtained. Thereby, from this membrane potential change (Vr'−Vr), the aftertaste can be determined as a CPA (Change of membrane Potential by Adsorption) value. The results obtained at the time of using a 0.3 mmol/L tartaric acid solution containing 30 mmol/L potassium chloride as a reference solution are used as the measured values.

There are no particular limitations on the environmental temperature at the time of measurement; however, it is preferable that the measurement is carried out at room temperature (1° C. to 30° C.), normal temperature (15° C. to 25° C.), standard temperature (20° C.), or the like as defined in the Japanese Pharmacopeia.

According to the present disclosure, the foretaste is the taste felt immediately after a food is taken into the mouth, and in a case in which the foretaste is evaluated as a taste item by the above-described measurement, the foretaste is expressed as "sour taste", "bitter taste and odd taste", "astringent taste and stimulation", "umami taste", and "salty taste". On the other hand, the aftertaste is the taste remaining in the tongue even after the food is swallowed, and in a case in which the aftertaste is evaluated as a taste item by the above-described measurement, the aftertaste is expressed as "bitter taste", "astringent taste", or "umami taste and richness".

The taste sensor that can be used for the present disclosure is not particularly limited; however, it is preferable to use a taste sensor having high responsiveness to the above-mentioned five basic tastes, and above all, it is more preferable to use a taste sensor having high responsiveness to sour taste, salty taste, bitter taste, umami taste, and astringent taste, from the viewpoint of analyzing the causes of the odor and bitter taste characteristic of *Salacia* genus plants, which significantly affect the flavor. Furthermore, the taste items obtained as the foretaste and/or aftertaste described above can also be used for the evaluation.

Regarding a commercially available measuring apparatus, for example, a taste perception apparatus, TS-5000Z (Intelligent Sensor Technology, Inc.), may be mentioned.

From the viewpoint of reducing the causes of the odor and bitter taste characteristic of *Salacia* genus plants, which significantly affect the flavor, the purified *Salacia* genus plant extract of the present disclosure is preferably such that the bitter taste and odd taste in the foretaste is 17.00 or less, the astringent taste and stimulation in the foretaste is 2.60 or less, the bitter taste in the aftertaste is 7.00 or less, and the astringent taste in the aftertaste is 1.50 or less. As these values are smaller, a purified *Salacia* genus plant extract giving a reduced level of taste that gives unpleasant feeling to the consumers is obtained, and therefore, there are no particular limitations on the lower limits.

[Use Applications]

The use of the purified *Salacia* genus plant extract of the present disclosure is not particularly limited as long as it is to provide the effects of the present invention, and examples include food products (including beverages and supplements), food materials, quasi-drugs, pharmaceutical products, pharmaceutical materials, and quasi-drug materials. Specifically, the description of paragraphs 0031 to 0060 of JP2017-132763A may be mentioned. In a case in which he purified *Salacia* genus plant extract of the present disclosure is applied to a food product, a food material, a quasi-drug for oral intake, a pharmaceutical product, a pharmaceutical material, and a quasi-drug material, the effects of the present disclosure act more effectively.

EXAMPLES

Hereinafter, the present invention will be described more specifically by way of Examples; however, the invention is not intended to be limited to the following Examples as long as the gist is maintained.

Example 1

I. Preparation of *Salacia* Genus Plant Extract

The root parts of *Salacia reticulata* were ground and then extracted with hot water at 70° C., a solution thus obtained was concentrated, and a *Salacia* genus plant-containing raw material extract (solid content concentration 10 to 15 mass %) was obtained.

II. Production of Purified *Salacia* Genus Extract

1) To the *Salacia* genus plant-containing raw material extract prepared in the procedure of I., 1.0 mass % of the activated carbon described in Example 1 of Table 1 was added with stirring, and thereby a mixed solution was obtained. The mixed solution thus obtained was heated to 50 degrees while being stirred, and an extraction step was carried out by causing the mixed solution to react with the activated carbon for 60 minutes under stirring.

2) After the reaction, filtration and centrifugation (rotation speed: 1,050 rpm, time: 10 minutes) were carried out, and a supernatant of the mixed solution was collected. Subsequently, the supernatant was subjected to concentration and spray drying, and thus a purified *Salacia* genus plant extract was obtained.

Examples 2 to 13 and Comparative Examples 2 and 3 were produced in the same manner as in Example 1, except that the type and concentration of the activated carbon, the treatment temperature, and the treatment time were changed as described in the following tables.

Comparative Example 1 was produced in the same manner as in Example 1, except that the extraction step described in II. 1) was not carried out.

[Evaluation]

For the purified *Salacia* genus plant extracts of Examples and Comparative Examples, the following various evaluations were carried out. The results are presented in the following tables.

1. Recovery Rate

While the recovery rate of Comparative Example 1 was taken as 100 mass %, the recovery rates of Examples 1 to 13 and Comparative Examples 2 and 3 were calculated.

2. Salacinol Concentration

The salacinol concentrations of Examples 1 to 13 and Comparative Examples 1 to 3 were measured by the Experiment method 1 described above. Subsequently, while the salacinol concentration of Comparative Example 1 was taken as 100 mass %, the salacinol concentrations of Examples and Comparative Examples were calculated.

3. Salacinol Recovery Rate

The salacinol recovery rates of Examples and Comparative Examples were calculated on the basis of the following formula.

Salacinol recovery rate (%)=recovery rate (%)×salacinol concentration

4. α-Glucosidase Inhibitory Activity

The sucrase $IC_{50}$ values of Examples and Comparative Examples were measured by the Experiment method 1 described above. Subsequently, the α-glucosidase inhibitory activity of Examples and Comparative Examples was calculated on the basis of the following formula.

α-Glucosidase inhibitory activity (%)={(1/sucrase $IC_{50}$ value of each of Examples and Comparative Examples)/(1/$IC_{50}$ value of Comparative Example 1)}×100

5. Evaluation of Odor

An evaluation was carried out by five test subjects by the following procedure.

1) Comparative Example 1 was taken as criterion 5, and the respective test subjects evaluated according to the following criteria.

1: The odor characteristic of *Salacia* genus plants is not perceived, and the composition can be orally taken in easily.

2: The odor characteristic of *Salacia* genus plants is slightly perceived; however, there is no problem for oral intake.

3. The odor characteristic of *Salacia* genus plants is perceived but can be orally taken in.

4. The odor characteristic of *Salacia* genus plants is slightly strongly perceived, and oral intake thereof is difficult.

5: The odor characteristic of *Salacia* genus plants is strongly perceived, and oral intake thereof is very difficult.

2) The values of 1) were arithmetically averaged for each of Examples and Comparative Examples, and the values were evaluated according to the following criteria.

A: 1.0 or higher and lower than 2.0
B: 2.0 or higher and lower than 3.0
C: 3.0 or higher and lower than 4.0
D: 4.0 or higher and 5.0 or lower Meanwhile, A, B, or C is in the range of being acceptable as a manufactured product.

6. Evaluation of bitter taste

An evaluation was carried out by five test subjects by the following procedure.

1) Comparative Example 1 was taken as criterion 5, and the respective test subjects evaluated according to the following criteria.

1: Bitter taste is not perceived, and the composition can be orally taken in easily.

2: Bitter taste is slightly perceived; however, there is no problem for oral intake.

3. Bitter taste is perceived but can be orally taken in.

4. Bitter taste is slightly strongly perceived, and oral intake thereof is difficult.

5: Bitter taste is strongly perceived, and oral intake thereof is very difficult.

2) The values of 1) were arithmetically averaged, and the values were evaluated according to the following criteria.

A: 1.0 or higher and lower than 2.0
B: 2.0 or higher and lower than 3.0

C: 3.0 or higher and lower than 4.0
D: 4.0 or higher and 5.0 or lower
Meanwhile, A, B, or C is in the range of being acceptable as a manufactured product.

7. Evaluation of Coloration

A sample was dissolved in pure water to a concentration of 0.7%, and the absorbance at a wavelength of 550 nm was measured by ultraviolet-visible spectroscopy using a cell having an optical path length of 1 cm.

An ultraviolet-visible spectrophotometer (model name: U-3310, Hitachi, Ltd.) was used as the measuring apparatus, and pure water was used for a blank test.

8. Content Ratio of Polyphenol (Epicatechin)

The content of epicatechin in each of Examples 1 to 13 and Comparative Examples 1 to 3 was measured by a HPLC-mass analysis method. While Comparative Example 1 was taken as 100, the content ratios of epicatechin of Examples 1 to 13, Comparative Example 2, and Comparative Example 3 were calculated.

9. Measurement of Content (Mass %) of Polyphenol (Epicatechin)

The content of polyphenol (epicatechin) in a composition was quantitatively determined by detecting by high-performance liquid chromatography under the following conditions.

Column: LiChrosorb RB-18
Flow rate: 1 mL/min
Eluent: Liquid A, 0.05 M phosphoric acid; liquid B, 0.05 M phosphoric acid solution containing 40% acetonitrile
Gradient: An eluent of "A:B=80:20" was changed to "A:B=30:70" over the range of after 10 minutes to after 60 minutes.
Oven temperature: 30° C.
Injection amount: 5 μL
Conditions for detector: Absorbance at 280 nm 10. Evaluation of Storage Stability Over Time A sample was encapsulated in a sample bottle and stored for one month in an atmosphere of 40° C., and then the generation of coloration and an odor after a lapse of time were evaluated by the following procedure.

10-1. Evaluation of Generation of Coloration

The coloration of the sample after storage was evaluated by a procedure similar to "7. Evaluation of coloration" as described above.

10-2. Evaluation of Generation of Odor

The odor of the sample after storage was evaluated by a procedure similar to "5. Evaluation of odor" as described above.

TABLE 1

| | | | | Example 1 | Example 2 | Example 3 | Example 4 |
|---|---|---|---|---|---|---|---|
| Activated carbon | Concentration (mass %) | | | 1.00 | 1.00 | 1.00 | 1.00 |
| | Average pore diameter (nm) | | | 3.4 | 1.5 | 7.0 | 4.5 |
| | Specific surface area (m²/g) | | | 1250 | 1500 | 1400 | 1700 |
| | Treatment temperature | | | 50° C. | 50° C. | 50° C. | 50° C. |
| | Treatment time | | | 60 min | 60 min | 60 min | 60 min |
| Evaluation | Recovery rate (mass %) | | | 78 | 79 | 67 | 97 |
| | α-Glucosidase inhibitory activity (%) | | | 104 | 104 | 109 | 102 |
| | Salacinol concentration (mass %) | | | 105 | 104 | 108 | 99 |
| | Salacinol recovery rate (%) | | | 82 | 82 | 72 | 96 |
| | Odor | | | B | B | B | B |
| | Bitter taste | | | B | C | C | B |
| Evaluation | Content ratio of polyphenol (epicatechin) (mass %) | | | 62 | 99 | 32 | 67 |
| | Content of polyphenol (epicatechin) (mass %) | | | 0.0022 | 0.0036 | 0.0012 | 0.0024 |
| | Coloration | Before time lapse | | 1.01 | 0.87 | 0.83 | 1.11 |
| | | After time lapse | | 1.02 | 0.91 | 0.87 | 1.05 |
| | Odor | Before time lapse | | B | B | B | B |
| | | After time lapse | | B | B | B | B |

| | | | | Example 5 | Example 6 | Example 7 | Example 8 |
|---|---|---|---|---|---|---|---|
| Activated carbon | Concentration (mass %) | | | 5.00 | 7.00 | 7.00 | 7.00 |
| | Average pore diameter (nm) | | | 4.5 | 4.5 | 4.5 | 1.8 |
| | Specific surface area (m²/g) | | | 1700 | 1700 | 1700 | 1530 |
| | Treatment temperature | | | 50° C. | 50° C. | 50° C. | 50° C. |
| | Treatment time | | | 60 min | 60 min | 120 min | 120 min |
| Evaluation | Recovery rate (mass %) | | | 91 | 86 | 85 | 77 |
| | α-Glucosidase inhibitory activity (%) | | | 102 | 109 | 115 | 109 |
| | Salacinol concentration (mass %) | | | 102 | 106 | 133 | 111 |
| | Salacinol recovery rate (%) | | | 93 | 91 | 114 | 85 |
| | Odor | | | A | A | A | B |
| | Bitter taste | | | A | A | A | B |
| Evaluation | Content ratio of polyphenol (epicatechin) (mass %) | | | 0 | 0 | 0 | 19 |
| | Content of polyphenol (epicatechin) (mass %) | | | 0.0000 | 0.0000 | 0.0000 | 0.0007 |
| | Coloration | Before time lapse | | 1.04 | 1.05 | 1.10 | 1.15 |
| | | After time lapse | | 1.02 | 0.99 | 1.01 | 1.16 |
| | Odor | Before time lapse | | A | A | A | B |
| | | After time lapse | | A | A | A | B |

TABLE 2

| | | Example 9 | Example 10 | Example 11 | Example 12 |
|---|---|---|---|---|---|
| Activated carbon | Concentration (mass %) | 7.00 | 7.00 | 7.00 | 7.00 |
| | Average pore diameter (nm) | ※ | 4.5 | 4.5 | 4.5 |
| | Specific surface area (m²/g) | 1900 | 1700 | 1700 | 1700 |
| | Treatment temperature | 50° C. | 50° C. | 50° C. | 10° C. |
| | Treatment time | 120 min | 1 min | 360 min | 120 min |
| Evaluation | Recovery rate (mass %) | 92 | 83 | 81 | 79 |
| | α-Glucosidase inhibitory activity (%) | 101 | 100 | 109 | 109 |
| | Salacinol concentration (mass %) | 93 | 89 | 114 | 113 |
| | Salacinol recovery rate (%) | 86 | 74 | 92 | 89 |
| | Odor | B | B | B | B |
| | Bitter taste | B | B | B | B |
| Evaluation | Content ratio of polyphenol (epicatechin) (mass %) | 17 | 0 | 0 | 0 |
| | Content of polyphenol (epicatechin) (mass %) | 0.0011 | 0.0000 | 0.0000 | 0.0000 |
| | Coloration — Before time lapse | 1.20 | 1.19 | 1.36 | 1.20 |
| | Coloration — After time lapse | 1.23 | 1.21 | 1.36 | 1.21 |
| | Odor — Before time lapse | B | B | B | B |
| | Odor — After time lapse | B | B | B | B |

| | | Example 13 | Comparative Example 1 | Comparative Example 2 | Comparative Example 3 |
|---|---|---|---|---|---|
| Activated carbon | Concentration (mass %) | 7.00 | — | 0.01 | 30.00 |
| | Average pore diameter (nm) | 4.5 | — | 4.5 | 4.5 |
| | Specific surface area (m²/g) | 1700 | — | 1700 | 1700 |
| | Treatment temperature | 100° C. | — | 50° C. | 50° C. |
| | Treatment time | 120 min | — | 120 min | 120 min |
| Evaluation | Recovery rate (mass %) | 86 | 100 | 94 | 46 |
| | α-Glucosidase inhibitory activity (%) | 100 | 100 | 95 | 100 |
| | Salacinol concentration (mass %) | 79 | 100 | 68 | 99 |
| | Salacinol recovery rate (%) | 68 | 100 | 64 | 46 |
| | Odor | B | D | C | B |
| | Bitter taste | B | D | C | B |
| Evaluation | Content ratio of polyphenol (epicatechin) (mass %) | 28 | 100 | 100 | 0 |
| | Content of polyphenol (epicatechin) (mass %) | 0.0010 | 0.0036 | 0.0036 | 0.0000 |
| | Coloration — Before time lapse | 1.38 | 1.22 | 1.12 | 1.60 |
| | Coloration — After time lapse | 1.38 | 1.26 | 1.14 | 1.61 |
| | Odor — Before time lapse | B | D | C | B |
| | Odor — After time lapse | B | D | C | B |

※ KURARAY COAL (registered trademark) GLC (Kuraray Co., Ltd.): Mixture of average pore diameters of 4 to 20 nm From the above results, Examples 1 to 13 all exhibited high recovery rates while having satisfactory effects of reducing the odor and bitter taste characteristic of *Salacia* genus plants. Furthermore, surprisingly, Examples 1 to 9, 11, and 12 exhibited satisfactory α-glucosidase inhibitory activity compared to Comparative Example 1 (sample that was not subjected to the extraction step using activated carbon of the present disclosure).

Example 1 and Examples 3 to 13 had very low content ratios of epicatechin among polyphenols, compared to Comparative Example 1. Therefore, it is considered that Examples 1 to 13 have satisfactory effects of ameliorating bitter taste as described in the tables. Furthermore, Examples 1 to 13 had the generation of coloration and odor suppressed even after a lapse of time and had satisfactory storage stability.

11. Evaluation of Flavor by Taste Sensor

For Examples 7 to 9 and Comparative Examples 1 to 3, an evaluation of flavor was carried out using taste sensors.

1) Preparation of Sample Solution 100 g of water was added to 1.2 g of a sample, and the mixture was stirred. This was used as a test solution for each case.

As a reference solution, a 0.3 mmol/L tartaric acid solution containing 30 mmol/L potassium chloride was prepared.

2) Measurement and Evaluation in Taste Perception Apparatus

An analysis of the taste of the test solution was carried out using a taste perception apparatus according to the measurement conditions described below. That is, five items of the foretaste (sour taste, bitter taste and odd taste, astringent taste and stimulation, umami taste, and salty taste) and three items of the aftertaste (bitter taste, astringent taste, and umami taste and richness) were measured using five kinds of taste sensors. Specifically, the measurement potential in the reference solution of each of the five kinds of taste sensors was designated as zero, and the difference with the measurement potential in the test solution was designated as the foretaste. Subsequently, the respective taste sensors were washed with the reference solution, and the difference in the potential at the time of measuring the reference solution again was designated as the aftertaste.

For the analysis of the measurement results thus obtained, an analysis application affiliated to the apparatus was used.

<Measurement Conditions>

Taste perception apparatus: TS-5000Z (Intelligent Sensor Technology, Inc.)

Measurement temperature: Room temperature

Analysis application: Taste perception apparatus TS-5000Z Analysis Application Ver 1.6.5 (Intelligent Sensor Technology, Inc.)

Taste sensor: CA0, C00, AE1, AAE, CT0 (Intelligent Sensor Technology, Inc.)

Taste sensors of CA0, C00, AE1, AAE, and CT0 were used, and the taste sensors were allowed to judge the taste. The content of determination was converted to the various taste items as described below and then was outputted.

Conversion to various taste items

CA0: Sour taste (foretaste)

C00: Bitter taste and odd taste (foretaste), bitter taste (aftertaste)

AE1: Astringent taste and stimulation (foretaste), astringent taste (aftertaste)

AAE: Umami taste (foretaste), umami taste and richness (aftertaste)

CT0: Salty taste (foretaste)

As an index of the odor and bitter taste characteristic of *Salacia* genus plants, which significantly affect the flavor, measurement results on four types of taste items (bitter taste and odd taste in the foretaste, astringent taste and stimulation in the foretaste, bitter taste in the aftertaste, and astringent taste in the aftertaste) were evaluated. The results are presented in Table 3.

taste in the foretaste was 17.00 or less, the astringent taste and stimulation in the foretaste was 2.60 or less, the bitter taste in the aftertaste was 7.00 or less, and the astringent taste in the aftertaste was 1.50 or less, exhibited satisfactory results also in the evaluation results for odor or bitter taste provided by human beings.

The sample of Comparative Example 3 exhibited results of reduced odor and bitter taste characteristic of *Salacia* genus plants in the evaluation results for the flavor provided by taste sensors and the evaluation results of odor or bitter taste provided by human beings; however, since the flavor of activated carbon was felt, the sample was evaluated to be inappropriate for oral intake.

What is claimed is:

1. A method for producing a purified *Salacia* genus plant extract, the method comprising an extraction step of bringing a *Salacia* genus plant-containing raw material extract comprising at least one of a *Salacia* genus plant, a *Salacia* genus plant extract, or a *Salacia* genus plant ground product, into contact with 0.1 to 20 mass % of activated carbon in the presence of an extraction solvent, wherein the purified *Salacia* genus plant extract has a content of the sum of polyphenols and lipids of less than 10 mass % with respect to the total amount of the purified *Salacia* genus plant extract.

2. The method for producing a purified *Salacia* genus plant extract according to claim 1, wherein the time for bringing the *Salacia* genus plant-containing raw material extract into contact with the activated carbon is 5 minutes to 5 hours.

3. The method for producing a purified *Salacia* genus plant extract according to claim 1, wherein water at 10° C. to 100° C. is used as the extraction solvent.

4. The method for producing a purified *Salacia* genus plant extract according to claim 1, wherein the activated carbon has a specific surface area of 500 to 2,500 m$^2$/g and an average pore diameter of 0.5 to 10 nm.

TABLE 3

|  |  |  | Example 7 | Example 8 | Example 9 | Comparative Example 1 | Comparative Example 2 | Comparative Example 3 |
|---|---|---|---|---|---|---|---|---|
| Evaluation | Odor |  | A | B | B | D | C | B |
|  | Bitter taste |  | A | B | B | D | C | B |
|  | Foretaste | Bitter taste and odd taste | 6.44 | 16.70 | 8.73 | 19.65 | 19.14 | 2.10 |
|  |  | Astringent taste and stimulation | 1.07 | 2.05 | 1.25 | 3.01 | 3.02 | 0.25 |
|  | Aftertaste | Bitter taste | 0.47 | 6.54 | 1.42 | 8.45 | 8.60 | −0.35 |
|  |  | Astringent taste | 0.83 | 1.25 | 0.95 | 1.57 | 1.55 | 0.58 |

From the above results, the evaluation results for the flavor provided by taste sensors (four types of taste items) and the results of performing an evaluation in 5. Evaluation of odor and 6. Evaluation of bitter taste were found to be correlated. Specifically, the purified *Salacia* genus plant extracts of Examples 7 to 9, in which the bitter taste and odd 5. The method for producing a purified *Salacia* genus plant extract according to claim 1, wherein the content of epicatechin with respect to the total amount of the purified *Salacia* genus plant extract is less than 0.004 mass %.

* * * * *